US008389758B2

(12) United States Patent
Gorodisher et al.

(10) Patent No.: US 8,389,758 B2
(45) Date of Patent: *Mar. 5, 2013

(54) BENZOXAZINE-THIOL ADDUCTS

(75) Inventors: Ilya Gorodisher, Stillwater, MN (US);
Robert J. Webb, Hudson, WI (US);
Robert J. Devoe, Arden Hills, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 512 days.

This patent is subject to a terminal disclaimer.

(21) Appl. No.: 12/685,703

(22) Filed: Jan. 12, 2010

(65) Prior Publication Data
US 2010/0312004 A1 Dec. 9, 2010

Related U.S. Application Data

(60) Provisional application No. 61/184,328, filed on Jun. 5, 2009.

(51) Int. Cl.
*C27C 321/00* (2006.01)
*C09B 11/02* (2006.01)
*C09J 5/00* (2006.01)
*C08G 75/04* (2006.01)
*B65C 9/25* (2006.01)

(52) U.S. Cl. .......... 560/16; 564/323; 564/341; 156/311; 156/322; 528/374

(58) Field of Classification Search .......... 560/16; 564/341, 323; 156/311, 322; 528/374
See application file for complete search history.

(56) References Cited

U.S. PATENT DOCUMENTS

| 1,965,776 | A | 7/1937 | Lantz |
| 3,653,959 | A | 4/1972 | Kehr |
| 3,682,948 | A | 8/1972 | Tomalia et al. |
| 4,118,377 | A | 10/1978 | D'Alelio |
| 4,503,211 | A | 3/1985 | Robins |
| 4,846,905 | A | 7/1989 | Tarbutton et al. |
| 5,543,516 | A | 8/1996 | Ishida |
| 5,554,664 | A | 9/1996 | Lamanna et al. |
| 5,910,521 | A | 6/1999 | Johnson et al. |
| 5,973,144 | A | 10/1999 | Ishida |
| 6,160,079 | A | 12/2000 | Ishida et al. |
| 6,207,786 | B1 | 3/2001 | Ishida et al. |
| 6,225,440 | B1 | 5/2001 | Ishida |
| 6,323,270 | B1 | 11/2001 | Ishida |
| 6,376,080 | B1 | 4/2002 | Gallo |
| 6,482,946 | B1 | 11/2002 | Dettloff et al. |
| 6,620,905 | B1 | 9/2003 | Musa |
| 6,635,689 | B1 | 10/2003 | Mahoney et al. |

(Continued)

FOREIGN PATENT DOCUMENTS

EP 0 477 789 4/1992
WO WO 03/072638 9/2003

(Continued)

OTHER PUBLICATIONS

Riess G. et. al, Advances in Polymer Science: Polymer Science and Technology, Ring Opening Polymerization of Benzoxazines: vol. 31, 1985.*

(Continued)

*Primary Examiner* — John J Figueroa
*Assistant Examiner* — Atnaf Admasu
(74) *Attorney, Agent, or Firm* — Kent S. Kokko

(57) ABSTRACT

Novel benzoxazine-thiol adducts are described, which may be may be cured to produce compositions useful in coating, sealants, adhesive and many other applications.

21 Claims, 1 Drawing Sheet

U.S. PATENT DOCUMENTS

| | | |
|---|---|---|
| 6,743,852 B2 | 6/2004 | Dershem et al. |
| 6,899,960 B2 | 5/2005 | Shi et al. |
| 7,041,772 B2 | 5/2006 | Aizawa et al. |
| 7,053,138 B2 | 5/2006 | Magendie et al. |
| 7,157,509 B2 | 1/2007 | Li et al. |
| 7,179,684 B2 | 2/2007 | Shi et al. |
| 7,202,359 B2 | 4/2007 | Hwang et al. |
| 7,452,585 B1 | 11/2008 | Wong et al. |
| 7,517,925 B2 | 4/2009 | Dershem et al. |
| 2009/0240003 A1 | 9/2009 | Burns et al. |

FOREIGN PATENT DOCUMENTS

| | | |
|---|---|---|
| WO | WO 2007/064801 | 6/2007 |
| WO | WO 2008/034814 | 3/2008 |
| WO | WO 2009/075744 | 6/2009 |
| WO | WO 2009/115586 | 9/2009 |

OTHER PUBLICATIONS

Rimdusit, et al., "Development of New Class of Electronic Packaging Materials Based on Ternary Systems of Benzoxazine, Epoxy, and Phenolic Resins," Polymer, vol. 41, Issue 22, pp. 7941-7949, (2000).

Kirmura, et al., "New Thermosetting Resin from Bisphenol A-based Benzoxazine and Bisoxazoline," Journal of Applied Science, vol. 72, Issue 12, pp. 1551-1558, (1999).

Ghosh, et al., "Polybenzoxazine—New high performance thermosetting resins: Synthesis and properties," Progress in Polymer Science, vol. 32, pp. 1344-1391, (2007).

Kostka, et al., "The Reactions of Diethyl 2,3-Dihydro-4H-1,3-Benzoxazin-4-One-2-Phosphonate With Nucleophiles," Phosphorus, Sulfur and the Related Elements, vol. 83, pp. 215-221, (1993).

Cid, et al., "Cationic Polymerization of Benzoxazine Monomers by Boron Trifluoride Complex," Polymers & Polymer Composites, vol. 7, No. 6, pp. 409-420, (1999).

Wang, et al., "Cationic ring-opening polymerization of benzoxazines," Polymer, vol. 40, pp. 4563-4570, (1999).

Ishida, et al., "Curing kinetics of a new benzoxazine-based phenolic resin by differential scanning calorimetry," Polymer, vol. 36, No. 16, pp. 3151-3158, (1995).

Dunkers, et al., "Reaction of Benzoxazine-Based Phenolic Resins with Strong and Weak Carboxylic Acids and Phenols as Catalysts," Journal of Polymer Science: Part A: Polymer Chemistry, vol. 37, pp. 1913-1921, (1999).

Ishida, et al., "Catalyzing the Curing Reaction of a New Benzoxazine-Based Phenolic Resin," Journal of Applied Polymer Science, vol. 58, pp. 1751-1760, (1995).

Espinosa, et al., "Synthesis and Characterization of Benzoxazine-Based Phenolic Resins: Crosslinking Study," Journal of Applied Polymer Science, vol. 90, pp. 470-481, (2003).

Perez et al., "The Reduction of 2,4-Dihydroxy-7-Methoxy-1,4-Benzoxazin-3-One by Thiols," Phytochemistry, vol. 24, No. 12, pp. 2963-2966, 1985.

PCT International Search Report, PCT/US2010/036795, Sep. 12, 2010.

PCT International Search Report, PCT/US2010/036796, Sep. 12, 2010.

* cited by examiner

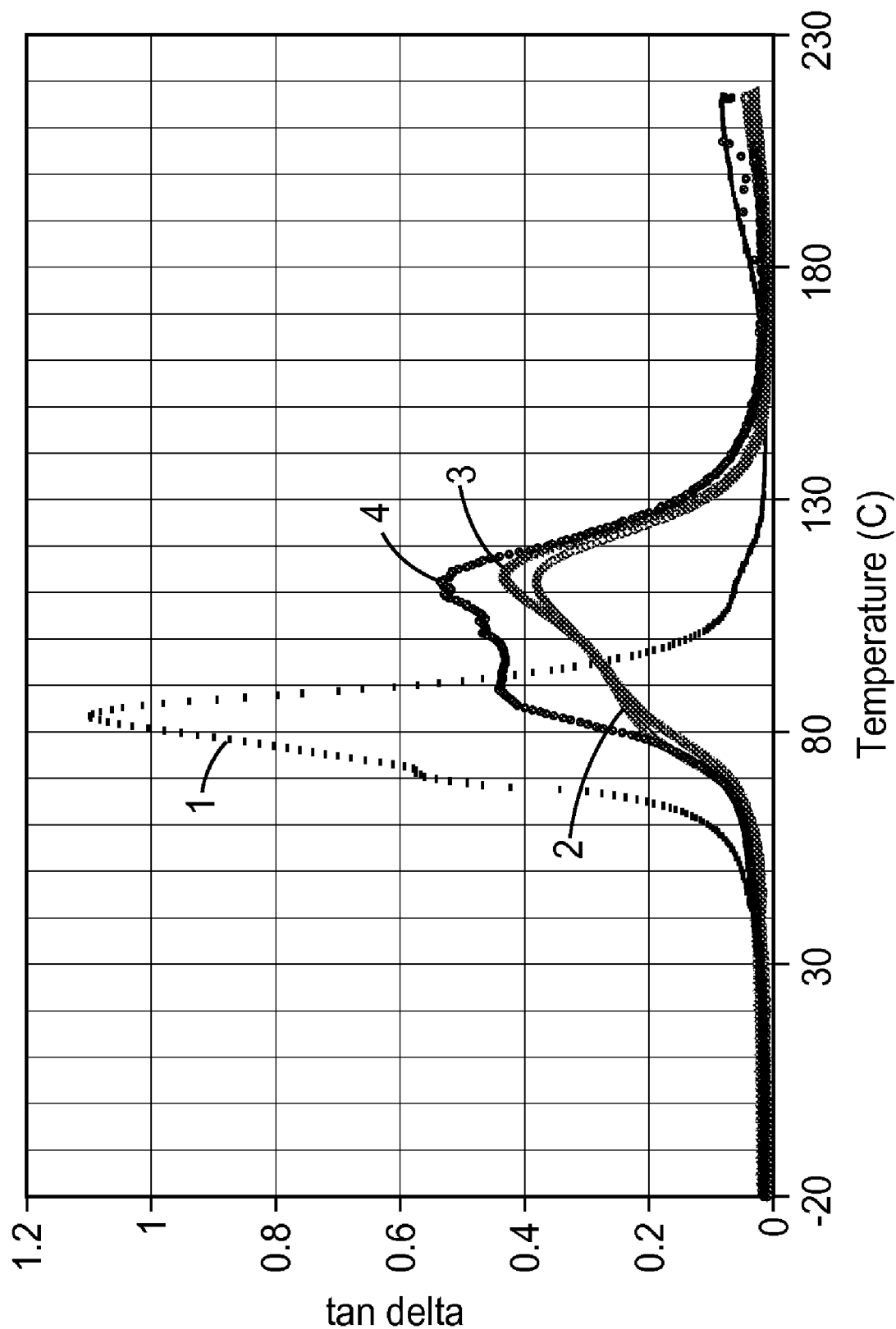

BENZOXAZINE-THIOL ADDUCTS

CROSS REFERENCE TO RELATED APPLICATION

This application claims the benefit of U.S. Provisional Patent Application No. 61/184,328, filed Jun. 5, 2009, the disclosure of which is incorporated by reference herein in its entirety.

FIELD OF THE INVENTION

The present disclosure is directed to novel compounds and polymers derived from the reaction of benzoxazine compounds with thiol compounds. The compositions are useful in coating, sealants, adhesive and many other applications.

BACKGROUND

Benzoxazines and compositions containing benzoxazine are known (see for example, U.S. Pat. Nos. 5,543,516 and 6,207,786 to Ishida, et al.; S. Rimdusit and H. Ishida, "Development of New Class of Electronic Packaging Materials Based on Ternary Systems of Benzoxazine, Epoxy, and Phenolic Resins", Polymer, 41, 7941-49 (2000); and H. Kimura, et al., "New Thermosetting Resin from Bisphenol A-based Benzoxazine and Bisoxazoline", J. App. Polym. Sci., 72, 1551-58 (1999).

U.S. Pat. No. 7,517,925 (Dershem et al.) describes benzoxazine compounds and thermosetting resin compositions prepared therefrom. The compositions are said to be useful for increasing adhesion at interfaces within microelectronic packages and low shrinkage on cure and low coefficient of thermal expansion (CTE).

U.S. Pat. No. 7,053,138 (Magendie et al.) describes compositions comprising benzoxazines and thermoplastic or thermoset resins in the manufacture of prepregs and laminates. The compositions are said to yield flame-proofed laminating resins that have high glass transition temperatures.

U.S. Pat. No. 6,376,080 (Gallo) describes a method of preparing a polybenzoxazine which includes heating a molding composition including a benzoxazine and a heterocyclic dicarboxylic acid to a temperature sufficient to cure the molding composition, thereby forming the polybenzoxazine. The compositions are said to have near-zero volume change after post cure.

SUMMARY

The present disclosure is directed to novel benzoxazine-thiol adducts. Further, the present disclosure is directed to a method of preparing the adducts, which comprises reacting a benzoxazine compound with a thiol compound, the reaction resulting in ring-opening of the oxazine ring, and resulting in an sulfanylmethyl aminophenolic compound. The present benzoxazine-thiol adducts may be cured to produce cured compositions useful in coating, sealants, adhesive and many other applications. The present disclosure further provides a curable composition comprising a benzoxazine compound and a thiol compound, which when cured is useful in adhesive, coating and bonding applications.

In the process of preparing the benzoxazine-thiol adducts, each of the starting materials may be mono- or higher functionality. The benzoxazine may be a mono- or higher benzoxazine, and the thiol compound may be a mono- or higher thiol.

As used herein the term "benzoxazine" is inclusive of compounds and polymers having the characteristic benzoxazine ring. In the illustrated benzoxazine group, R is the residue of a mono- or polyamine.

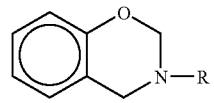

I

As used herein, "alkyl" includes straight-chained, branched, and cyclic alkyl groups and includes both unsubstituted and substituted alkyl groups. Unless otherwise indicated, the alkyl groups typically contain from 1 to 20 carbon atoms. Examples of "alkyl" as used herein include, but are not limited to, methyl, ethyl, n-propyl, n-butyl, n-pentyl, isobutyl, t-butyl, isopropyl, n-octyl, n-heptyl, ethylhexyl, cyclopentyl, cyclohexyl, cycloheptyl, adamantyl, and norbornyl and the like. Unless otherwise noted, alkyl groups may be mono- or polyvalent.

As used herein, the term "heteroalkyl" includes both straight-chained, branched, and cyclic alkyl groups with one or more heteroatoms independently selected from S, O, and N both unsubstituted and substituted alkyl groups. Unless otherwise indicated, the heteroalkyl groups typically contain from 1 to 20 carbon atoms. "Heteroalkyl" is a subset of "hetero(hetero)hydrocarbyl" described below. Examples of "heteroalkyl" as used herein include, but are not limited to methoxy, ethoxy, propoxy, 3,6-dioxaheptyl, 3-(trimethylsilyl)-propyl, 4-dimethylaminobutanyl, and the like. Unless otherwise noted, heteroalkyl groups may be mono- or polyvalent.

As used herein, "aryl" is an aromatic group containing 6-18 ring atoms and can contain fused rings, which may be saturated, unsaturated, or aromatic. Examples of an aryl group include phenyl, naphthyl, biphenyl, phenanthryl, and anthracyl. Heteroaryl is aryl containing 1-3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl. Unless otherwise noted, aryl and heteroaryl groups may be mono- or polyvalent.

As used herein "(hetero)hydrocarbyl" is inclusive of (hetero)hydrocarbyl alkyl and aryl groups, and hetero(hetero) hydrocarbyl heteroalkyl and heteroaryl groups, the later comprising one or more catenary oxygen heteroatoms such as ether or amino groups. Hetero(hetero)hydrocarbyl may optionally contain one or more catenary (in-chain) functional groups including ester, amide, urea, urethane and carbonate functional groups. Unless otherwise indicated, the non-polymeric (hetero)hydrocarbyl groups typically contain from 1 to 60 carbon atoms. Some examples of such (hetero)hydrocarbyls as used herein include, but are not limited to methoxy, ethoxy, propoxy, 4-diphenylaminobutyl, 2-(2'-phenoxyethoxy)ethyl, 3,6-dioxaheptyl, 3,6-dioxahexyl-6-phenyl, in addition to those described for "alkyl", "heteroalkyl", "aryl" and "heteroaryl" supra.

BRIEF DESCRIPTION OF THE FIGURES

FIG. 1 is a plot of the dynamic mechanical analysis scans of Example 11.

DETAILED DESCRIPTION

The present disclosure is directed to novel benzoxazine-thiol adducts. The benzoxazine-thiol adducts may be described sulfanylmethyl aminophenolic compounds, which may be monomeric, oligomeric or polymeric. Such compounds are prepared by the reaction of a benzoxazine with a thiol compound. The adducts are characterized as having the characteristic group resulting from ring opening of the oxazine ring with a thiol group. In the illustrated benzoxazine group, $R^5$ is the residue of a mono- or polyamine and $R^4$ is the residue of a mono- or polythiol, and $R^1$ is the residue of an aldehyde.

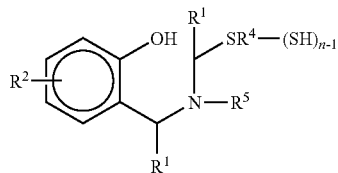

II wherein
each $R^1$ is H or an alkyl group, and is the residue of an aliphatic aldehyde,
$R^2$ is H, a covalent bond, or a polyvalent (hetero)hydrocarbyl group, preferably H, a covalent bond or a divalent alkyl group;
$R^4$ is the (hetero)hydrocarbyl residue of a thiol compound;
$R^5$ is the (hetero)hydrocarbyl residue of a primary amino compound, which may be a mono- or polyamine.

As used herein the term "residue" is used to define that (hetero)hydrocarbyl portion of a group remaining after removal (or reaction) of the attached functional groups, or the attached groups in a depicted formula. For example, the "residue" of butyraldehyde, $C_4H_9$—CHO is the monovalent alkyl $C_4H_9$—. The residue of hexamethylene diamine, $H_2N$—$C_6H_{12}$—$NH_2$ is the divalent alkyl—$C_6H_{12}$—. The residue of phenylene diamine $H_2N$—$C_6H_4$—$NH_2$, is the divalent aryl—$C_6H_4$—. The residue of diamino-polyethylene glycol, $H_2N$—$(C_2H_4O)_{1-20}$—$C_2H_4$—$NH_2$, is the divalent (hetero)hydrocarbyl polyethylene glycol—$(C_2H_4O)_{1-20}$—$C_2H_4$—.

In the preparation of the benzoxazine-thiol adducts, any benzoxazine compound may be used. Benzoxazines may be prepared by combining a phenolic compound, and aliphatic aldehyde, and a primary amine compound. U.S. Pat. No. 5,543,516 (Ishida), hereby incorporated by reference, describes a solventless method of forming benzoxazines. U.S. Pat. No. 7,041,772 (Aizawa et al.) describes a process for producing a benzoxazine resin which comprises the steps of reacting a phenol compound, an aldehyde compound and a primary amine in the presence of an organic solvent to synthesize a benzoxazine resin and removing generated condensation water and the organic solvent from a system under heating and a reduced pressure. Other suitable reaction schemes to produce mono-, di- and higher-functional benzoxazines are described in N. N. Ghosh et al., *Polybenzoxazine-new high performance thermosetting resins: synthesis and properties, Prog. Polym. Sci.* 32 (2007), pp. 1344-1391. One suitable method of producing the starting benzoxazine compounds is illustrated by the following reaction scheme:

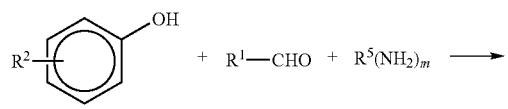

III

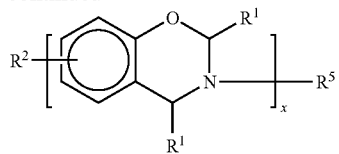

wherein
each $R^1$ is H or an alkyl group, and is the residue of an aliphatic aldehyde,
$R^2$ is H, a covalent bond, or a polyvalent (hetero)hydrocarbyl group, preferably H, a covalent bond or a divalent alkyl group;
$R^5$ is the (hetero)hydrocarbyl residue of a primary amino compound, $R^5(NH_2)_m$, where m is 1-4; and
x is at least 1.

A monophenol is illustrated for simplicity. Mono- or polyphenolic compounds may be used. The phenolic compound may be further substituted without limitation is desired. For example, the 3, 4, and 5 positions of the phenolic compound may be hydrogen or substituted with other suitable substituents such as alkyl, cycloalkyl, heterocycloalkyl, aryl, heteroaryl, aralkyl, heteroaralkyl, alkoxy, alkoxyalkylene, hydroxylalkyl, hydroxyl, haloalkyl, carboxyl, halo, amino, aminoalkyl, alkylcarbonyloxy, alkyloxycarbonyl, alkylcarbonyl, alkylcarbonylamino, aminocarbonyl, alkylsulfonylamino, aminosulfonyl, sulfonic acid, or alkylsulfonyl. Desirably at least one of the positions ortho to the hydroxyl group is unsubstituted to facilitate benzoxazine ring formation.

The aryl ring of the phenolic compound may be a phenyl ring as depicted, or may be selected from naphthyl, biphenyl, phenanthryl, and anthracyl. The aryl ring of the phenolic compound may further comprise a heteroaryl ring containing 1-3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

Examples or mono-functional phenols include phenol; cresol; 2-bromo-4-methylphenol; 2-allyphenol; 4-aminophenol; and the like. Examples of difunctional phenols (polyphenolic compounds) include phenolphthalein; biphenol, 4-4'-methylene-di-phenol; 4-4'-dihydroxybenzophenone; bisphenol-A; 1,8-dihydroxyanthraquinone; 1,6-dihydroxnaphthalene; 2,2'-dihydroxyazobenzene; resorcinol; fluorene bisphenol; and the like. Examples of trifunctional phenols comprise 1,3,5-trihydroxy benzene and the like.

With respect to the $R^2$ group of Formula II, numerous phenolic compounds are contemplated. $R^2$ may be an H, a covalent bond "—" which represents a biphenyl-type phenolic compounds, or $R^2$ may be a divalent aliphatic group linking aryl rings. For example, $R^2$ may be a divalent isopropyl group, derived from bisphenol-A, generally illustrated as follows:

III

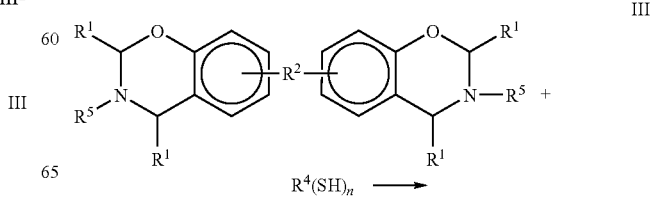

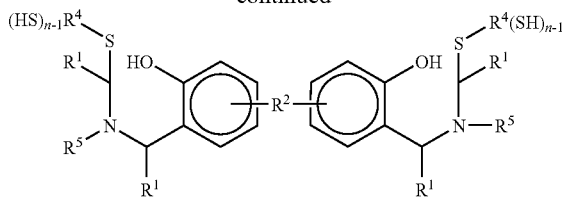

where
each $R^1$ is H or an alkyl group, and is the residue of an aliphatic aldehyde,
$R^2$ is H, a covalent bond, or a polyvalent (hetero)hydrocarbyl group, preferably H, a covalent bond or a divalent alkyl group;
$R^4$ is the (hetero)hydrocarbyl residue of a thiol compound;
$R^5$ is the (hetero)hydrocarbyl residue of a primary amino compound.

Note that Scheme III, and other schemes herein, the product depicts free thiol groups. The depiction is used to account for all the thiol groups present in the starting materials, which are available for subsequent reaction. Thus the starting bis-benzoxazine reacts with the polythiol $R^4(SH)_n$, and the initial reaction product has "n−1" thiol groups, which may be available for further reaction with additional benzoxazine groups. Further, the starting benzoxazine was prepared for a polyamine, therefore R5 groups may be connected to additional benzoxazine groups.

Note that in the above reaction scheme, monoamines and monothiols are depicted, however higher functional thiols and amines may also be used. It will be understood that the reaction of polybenzoxazines with a polythiol can provide polymeric materials such as:

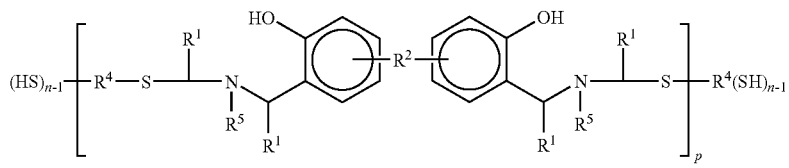

where
each $R^1$ is H or an alkyl group, and is the residue of an aliphatic aldehyde,
$R^2$ is H, a covalent bond, or a polyvalent (hetero)hydrocarbyl group, preferably H, a covalent bond or a divalent alkyl group;
$R^4$ is the (hetero)hydrocarbyl residue of a thiol compound;
$R^5$ is the (hetero)hydrocarbyl residue of a primary amino compound, and
p is at least one, preferably two or more.

The aldehyde reactants used in preparing the benzoxazine starting materials include formaldehyde; paraformaldehyde; polyoxymethylene; as well as aldehydes having the general formula $R^1CHO$, where $R^1$ is H or an alkyl group, including mixtures of such aldehydes, desirably having from 1 to 12 carbon atoms. The $R^1$ group may be linear or branched, cyclic or acyclic, saturated or unsaturated, or combinations thereof. Other useful aldehydes include crotonaldehyde; acetaldehyde; propionaldehyde; butyraldehyde; and heptaldehyde.

Amino compounds useful in preparing the starting benzoxazine can be substituted or unsubstituted, mono-, di-substituted or higher (hetero)hydrocarbyl amines having at least one primary amine group. The amines may be aliphatic or aromatic amines. It can be substituted, for example, with groups such as alkyl, cycloalkyl, heterocycloalkyl, aryl, heteroaryl, aralkyl, or heteroaralkyl. It has been observed that benzoxazines derived from aromatic amines, such as aniline, are less reactive toward the thiol reactants than benzoxazines derived from aliphatic amines as indicated, for example by the corresponding reaction temperatures, as illustrated in Example 13.

Amines useful in the preparation of the starting benzoxazine compounds include those of the formula $R^5(NH_2)_m$ include (hetero)hydrocarbyl monoamines and polyamines. $R^5$ may be (hetero)hydrocarbyl group that has a valence of m, and is the residue of a mono-, di- or higher amine having at least one primary amine group. $R^5$ can be an alkyl, a cycloalkyl or aryl and m 1 to 4. The $R^5$ is preferably selected from mono- and polyvalent (hetero)hydrocarbyl (i.e., alkyl and aryl compounds having 1 to 30 carbon atoms, or alternatively (hetero)hydrocarbyl including heteroalkyl and heteroaryl having 1 to twenty heteroatoms of oxygen.

In one embodiment, $R^5$ comprises a non-polymeric aliphatic, cycloaliphatic, aromatic or alkyl-substituted aromatic moiety having from 1 to 30 carbon atoms. In another embodiment, $R^5$ comprises a polymeric polyoxyalkylene, polyester, polyolefin, poly(meth)acrylate, polystyrene or polysiloxane polymer having pendent or terminal reactive —$NH_2$ groups. Useful polymers include, for example, amine-terminated oligo- and poly-(diaryl)siloxanes and (dialkyl)siloxane amino terminated polyethylenes or polypropylenes, and amino terminated poly(alkylene oxides).

Any primary amine may be employed. Useful monoamines include, for example, methyl-, ethyl-, propyl-, hexyl-, octyl, dodecyl-, dimethyl-, methyl ethyl-, and aniline. The term "di-, or polyamine," refers to organic compounds containing at least two primary amine groups. Aliphatic, aromatic, cycloaliphatic, and oligomeric di- and polyamines all are considered useful in the practice of the invention. Representative of the classes of useful di- or polyamines are 4,4'-methylene dianiline, 3,9-bis-(3-aminopropyl)-2,4,8,10-tetraoxaspiro[5,5]undecane, and polyoxyethylenediamine. Useful diamines include N-methyl-1,3-propane diamine; N-ethyl-1,2-ethanediamine; 2-(2-aminoethylamino)ethanol; pentaethylenehexaamine; ethylenediamine; N-methylethanolamine; and 1,3-propanediamine.

Examples of useful polyamines include polyamines having at least three amino groups, wherein at least one of the three amino groups are primary, and the remaining may be primary, secondary, or a combination thereof. Examples include $H_2N(CH_2CH_2NH)_{1-10}H$, $H_2N(CH_2CH_2CH_2CH_2NH)_{1-10}H$, $H_2N(CH_2CH_2CH_2CH_2CH_2CH_2NH)_{1-10}H$, $H_2N(CH_2)_3NHCH_2CH=CHCH_2NH(CH_2)_3NH_2$, $H_2N(CH_2)_4NH(CH_2)_3NH_2$, $H_2N(CH2)_3NH(CH_2)_4NH(CH_2)_3NH_2$, $H_2N(CH_2)_3NH(CH_2)2NH(CH_2)_3NH_2$, $H_2N(CH_2)_2NH(CH_2)_3NH(CH_2)_2NH_2$, $H_2N(CH_2)_3NH(CH_2)_2NH_2$, $C_6H_5NH(CH_2)_2NH(CH_2)_2NH_2$, and $N(CH_2CH_2NH_2)_3$, and polymeric polyamines such as linear or branched (including dendrimers) homopolymers and copolymers of ethyleneimine (i.e., aziridine). Many such compounds can be obtained, or are available, from general chemical suppliers such as, for example, Aldrich Chemical Company, Milwaukee, Wis. or Pfaltz and Bauer, Inc., Waterbury, Conn.

Many di- and polyamines, such as those just named, are available commercially, for example, those available from Huntsman Chemical, Houston, Tex. The most preferred di- or polyamines include aliphatic di- and triamines or aliphatic di- or polyamines and more specifically compounds with two or three primary amino groups, such as ethylene diamine, hexamethylene diamine, dodecanediamine, and the like.

Other useful amines include amino acids such as glycine, alanine, and leucine and their methyl esters, aminoalcohols such as ethanolamine, 3-aminopropanol, and 4-aminobutanol, polyaminoethers containing ethylene glycol and diethylene glycol (such as Jeffamine™ diamines), and alkenyl amines such as diallylamine and allylmethylamine.

It will be understood that monoamines will cyclize with the aldehyde and phenolic compound to produce mono-benzoxazine compounds, while di- or higher amines will cyclize to produce di- and poly-benzoxazine compounds: For example, a diamine (m=2 in the Scheme below) will produce a di-benzoxazine.

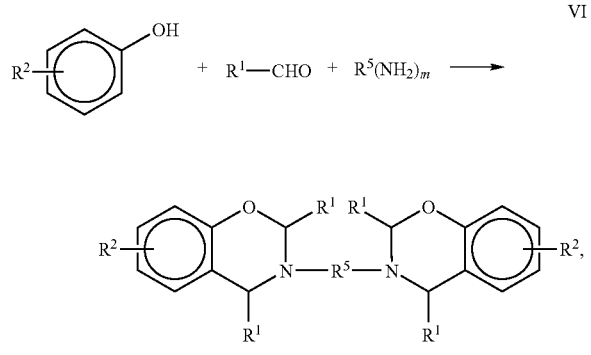

VI wherein each $R^1$ is H or an alkyl group, and is the residue of an aliphatic aldehyde;

$R^2$ is H, a covalent bond, or a polyvalent (hetero)hydrocarbyl group, preferably H, a covalent bond or a divalent alkyl group;

$R^5$ is the (hetero)hydrocarbyl residue of a primary amino compound.

Further, polymeric benzoxazines may be prepared from a polyphenolic compound, such as bisphenol-A, and a di- or polyamine. These polybenzoxazines may be ring-opened with a thiol compound, as previous described

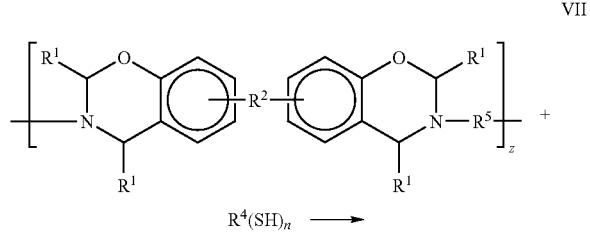

VII

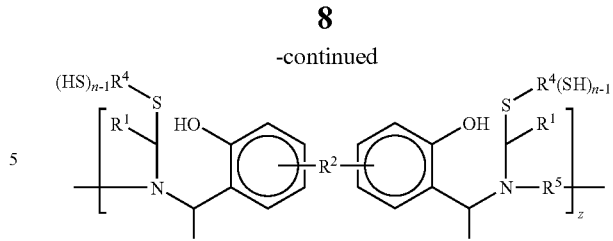

wherein
each $R^1$ is H or an alkyl group, and is the residue of an aliphatic aldehyde,
$R^2$ is H, a covalent bond, or a polyvalent (hetero)hydrocarbyl group, preferably H, a covalent bond or a divalent alkyl group;
$R^4$ is the (hetero)hydrocarbyl residue of a thiol compound;
$R^5$ is the (hetero)hydrocarbyl residue of a primary amino compound;
z is at least 1, preferably 2 or greater.

The benzoxazine ring is opened with thiols of the formula $R^4$—$(SH)_n$, where n is 1 to 6. $R^4$ includes any (hetero)hydrocarbyl groups, including aliphatic and aromatic monothiols and polythiols. $R^4$ may optionally further include one or more functional groups including hydroxyl, acid, ester, cyano, urea, urethane and ether groups.

In some preferred embodiments, the thiol compounds are of the formula:

$$R^6-[(CO_2)_x-R^7-SH]_y,$$ IX where $R^6$ is an alkylene group, an aryl group, an oxyalkylene group, or combination thereof,
$R^7$ is a divalent hydrocarbyl group, x is 0 or 1,
y is 1 to 6.

Useful thiol compounds falling within the scope of Formula IX include thiols is of the formulas:

X $$R^6+(O\overset{O}{\underset{\|}{-C}})_x R^7-SH]_y,$$

XI $$R^6+(\overset{O}{\underset{\|}{C}}-O)_x R^7-SH]_y, \text{ and}$$

XII $$R^6+R^7-SH]_y$$

wherein
$R^6$ is an alkylene group, an aryl group, an oxyalkylene group, or combination thereof,
$R^7$ is a divalent hydrocarbyl group,
x is 0 or 1,
y is 1 to 6. Preferably the compounds of Formulas IX to XII are those in which R6 is an alkylene group.

Useful alkyl thiols include methyl, ethyl and butyl thiol, as well as 2-mercaptoethanol, 3-mercapto-1,2-propanediol, 4-mercaptobutanol, mercaptoundecanol, 2-mercaptoethylamine, 2,3-dimercaptopropanol, 3-mercaptopropyltrimethoxysilane, mercaptoalkanoic acids and esters thereof including mercaptoproionic acid, 2-chloroethanethiol, 2-amino-3-mercaptopropionic acid, dodecyl mercaptan, thiophenol, 2-mercaptoethyl ether, and pentaerythritol tetrathioglycolate. Specific examples of useful polythiols include dimercaptodiethyl sulfide; 1,6-hexanedithiol; 1,8-dimercapto-3,6-dithiaoctane; propane-1,2,3-trithiol; 1,2-bis

[(2-mercaptoethyl)thio]-3-mercaptopropane; tetrakis(7-mercapto-2,5-dithiaheptyl)methane; and trithiocyanuric acid.

Another useful class of polythiols includes those obtained by esterification of a polyol with a terminally thiol-substituted carboxylic acid (or derivative thereof such as esters or acyl halides) including α- or β-mercaptocarboxylic acids such as thioglycolic acid or β-mercaptopropionic acid or esters thereof. Useful examples of compounds thus obtained include ethylene glycol bis(thioglycolate), pentaerythritol tetrakis(3-mercaptopropionate), ethylene glycol bis(3-mercaptopropionate), trimethylolpropane tris(thioglycolate), trimethylolpropane tris(3-mercaptopropionate), pentaerythritol tetrakis(thioglycolate) pentaerythritol tetrakis(3-mercaptopropionate), all of which are commercially available. A specific example of a preferred polymeric polythiol is polypropylene ether glycol bis(3-mercaptopropionate) which is prepared from polypropylene-ether glycol (e.g. Pluracol™ P201, BASF Wyandotte Chemical Corp.) and 3-mercaptopropionic acid by esterification.

In some embodiments, useful thiols include those thiols derived from epoxy compounds. The polythiol may be derived from the reaction between H2S (or equivalent) and an epoxy resin having two or more functional groups and preferably having a molecular weight of less than 1000. For example, bifunctional epoxy resins, such as a bisphenol A epoxy resin and a bisphenol F epoxy resin, and novolak epoxy resins, such as a phenolic novolak epoxy resin and a cresol novolak epoxy resin, or amine epoxy resins, can be used. In addition, generally known polyfunctional epoxy resins, heterocycle-containing epoxy resins, and alicyclic epoxy resins can be used. These epoxy resins may be used alone or in combinations of two or more chemical types or molecular weight ranges.

A particularly useful polythiol is that derived from bisphenol-A diglycidyl ether, available as QX-11 from Japan Epoxy Resins, having a thiol equivalent weight of ~245 and the following general structure, where n is at least 1:

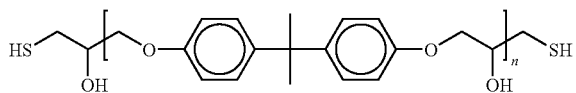

Useful soluble, high molecular weight thiols include polyethylene glycol di(2-mercaptoacetate), LP-3™ resins supplied by LP North America. (Houston, Tex.), and Permapol P3™ resins supplied by Products Research & Chemical Corp. (Glendale, Calif.) and compounds such as the adduct of 2-mercaptoethylamine and caprolactam.

As will be apparent to one skilled in the art, higher sulfanylmethyl aminophenolic compounds may be prepared using polythiols:

VIII

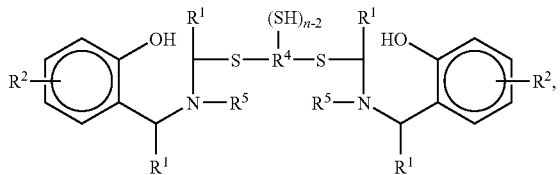

where
each $R^1$ is H or an alkyl group, and is the residue of an aliphatic aldehyde,
$R^2$ is H, a covalent bond, or a polyvalent (hetero)hydrocarbyl group, preferably H, a covalent bond or a divalent alkyl group;
$R^4$ is the (hetero)hydrocarbyl residue of a polythiol compound;
$R^5$ is the (hetero)hydrocarbyl residue of a primary amino compound.

The compounds of Formula II may be prepared by combining the benzoxazine compounds and the thiol compounds neat or in a suitable solvent. Suitable solvents include those in which the reactants dissolve, preferably at room temperature. Solvents may include that is non-reactive with the reactants and that provides for the subsequent dissolution of co-reactants. Examples of suitable solvents include butyl acetate, toluene, xylene, tetrahydrofuran, ethylene glycol dimethyl ether and the like. Heating is generally unnecessary as the thiol-induced ring opening is exothermic.

The stoichiometry of the reactants is not critical. Generally any molar ratio of benzoxazine to thiol may be used. Generally the molar amounts ratio of benzoxazine groups to thiol groups is about 1.1:1 to 1:1.1. In some embodiments it is preferable to have an excess of benzoxazine, as an unreacted benzoxazine will homopolymerize to form a coextensive mixture or polymer network of benzoxazine-thiol adduct and polybenzoxazines. In such embodiments, the molar amounts ratio of benzoxazine groups to thiol groups is about 1.1:1 to 50:1

If desired an acid catalyst may be used to promote the ring-opening of the benzoxazine. Suitable acid catalysts include, but are not limited to: strong inorganic acids such as hydrochloric acid, sulfuric acid, phosphoric acid, and the like; and organic acids such as acetic acid, para-toluene sulfonic acid, and oxalic acid. Acid catalysts may be used in amounts of 2 wt. % or less, preferably 1 wt. % or less, most preferably 0.5 wt. % or less, relative to the amounts of benzoxazine and thiol reactants.

The compositions may be used as coatings, including hard surface coatings, and pattern coatings; as adhesives, including pressure sensitive adhesives and structural adhesives; as sealants; and as coatings for electronics and other substrates. When uncured or partially cured, the benzoxazine compositions exhibit pressure-sensitive adhesive properties, including tack. In some embodiments, the present disclosure provides a coated article comprising a substrate, having a cured coating of the benzoxazine-thiol adduct thereon.

In some embodiments, the present disclosure provides "B-stagable" adhesives. Processing applications such as printed circuit manufacture often employ "stageable" adhesives, that is, adhesive compositions which can be partially cured to a tacky or tack-free coating, fastened to an adherend, and cured using heat, pressure, or both (see. U.S. Pat. No. 4,118,377). The tack-free state is sometimes referred to as the "B-Stage". Under ASTM Standard D907-91b "B-stage" means an intermediate stage in a thermosetting resin reaction in which the material softens when heated, and swells, but does not dissolve in certain liquids.

The present disclosure provides stagable adhesive compositions comprising a blend or mixture of thiol compound, benzoxazine compounds derived from an aromatic amine and benzoxazine compounds derived from an aliphatic amine. The stagable adhesive composition may further comprise an acid catalyst, as previously described. The stagable adhesive composition may be coated on to an adherend or substrate, and fully cured to a structural or semistructural adhesive using heat.

Upon combining the components the thiol compounds will preferentially react with the benzoxazine derived from an aliphatic amine to form a partially cured mixture. This partially cured mixture may be tacky or non-tacky at room temperature. On heating, the benzoxazine derived from an aromatic amine will react with the remaining thiol compounds to produce a fully cured adhesive.

The physical properties (e.g. viscosity, tack, peel, shear) of the uncured, B-staged, and cured compositions to be readily altered through the use of different amounts of each component: the thiol, the benzoxazine compounds derived from an aromatic amine and benzoxazine compounds derived from an aliphatic amine, or through the use of different species of the three components.

In some embodiments, the partially cured, stagable adhesive composition may be disposed between two substrates (or adherends), and subsequently heated to fully cure the adhesive and effect a structural or semistructual bond between the substrates. In other embodiments, the stagable adhesive composition may be heated to a flowable viscosity to effect coating of a substrate, which may then be joined to a second substrate while still molten and full curing effected.

In some embodiments, the present disclosure provides a method of assembling components using a thermally B-staged, further thermally curable, benzoxazine-based adhesive. In some embodiments, the thermal B-stage is accomplished by mild heating to promote partial reaction of the components of the stagable adhesive such that the viscosity increases sufficiently to allow coating. The thermal B-stage is followed by a thermal cure at a higher temperature. In some embodiments, the compositions of the present disclosure are useful for rapid assembly. The compositions of the present disclosure are particularly useful in assembly operations in which the adhesive desirably is colored or even opaque to a degree which would be difficult to attain in a system which is B-staged photochemically, for example by UV radiation, where the materials to be joined are opaque, or in which the required adhesive thickness is too great for easy photochemical curing.

"Mild heating" refers to heating the composition to a first temperature which is sufficient to initiate a chemical reaction between the adhesive components (in particular the benzoxazine derived from the aliphatic amine) to effect a combination of reaction to increase the viscosity of the composition to a desirable level for the B-stage. In some embodiments, the first temperature may be at or below 0° C. In some embodiments, the first temperature will be selected to be high enough to prevent premature viscosity increases prior to application to a substrate. In some embodiments, it may be desirable to store the adhesive composition at or below about 0° C. In other embodiments it would be protect the adhesive composition from exposure to temperatures above about 80° C. prior to application to the substrate. The first temperature will be lower than a second, higher temperature which is necessary to significantly initiate a secondary reaction between the adhesive components, i.e. the reaction of the thiol compound with the benzoxazine derived from an aromatic amine. In some embodiments, the temperature at which the adhesive composition is B-staged will be greater than about 90° C. In other embodiments, the temperature at which the adhesive composition is B-staged will be less than about 120° C.

It will be appreciated by those of skill in the art that the specific temperatures associated with the terms "first temperature" and "second, higher temperature" will, of necessity, depend upon the chemical components of a specific embodiment of the compositions of the invention and the properties of the materials to be bonded or adhered by the composition, the difference between the first, lower temperature and the second, higher temperature will generally be such that exposure to the first temperature is sufficient to produce the B-stage adhesive without significant advancement of the final cure mechanism or mechanisms. In some embodiments, the difference between the first temperature and the second, higher temperature will be at least about 25° C., preferably at least about 30° C. In other embodiments, the difference between the first temperature and the second, higher temperature will be no more than about 50° C., preferably no more than about 40° C. If the difference between the first, lower temperature and the second, higher temperature is too small, it may be difficult to limit the onset of the higher temperature cure reaction or reactions. If the difference between the first, lower temperature and the second, higher temperature is too large, the energy demands of the overall process may be undesirably high and damage to one or both of the materials to be joined may result. In some embodiments, the second, higher temperature will be greater than about 115° C., preferably greater than about 130° C. In other embodiments, the second, higher temperature will be no greater than about 150° C., preferably no greater than about 140° C.

In some preferred embodiments, the final thermal cure mechanism is a relatively slow reaction at the first temperature compared to the B-staging reaction that initially increases the viscosity of the resin. The relatively slower kinetics of this mechanism allow the same generic triggering event, heating, to initiate both reactions so that the adhesive composition is B-staged and tacky almost immediately after initial heating to a first temperature, but which does not fully cure until a later time at a second, higher temperature, allowing time for the substrate and adherent to be properly aligned before curing is complete. In some embodiments, the B-staged composition preferably is tacky enough to hold the substrate and adherent in place during the thermal cure without requiring known additional clamping means. In some embodiments, a final thermal cure at a second, higher temperature takes at least about 0.1 hours, preferably at least about 0.25 hour. In other embodiments, the final thermal cure requires no more than about 0.75 hours at the second, higher temperature, preferably no more than about 1.5 hours, to complete, allowing adequate time after initial heating to ensure that there is adequate contact between the adhesive composition, the substrate, and the adherent. In some embodiments, longer final thermal cure times at lower second, higher temperatures may be acceptable or even desirable.

Therefore the present disclosure provides stagable, structural and semi-structural adhesives. "Semi-structural adhesives" are those cured adhesives that have an overlap shear strength of at least about 0.5 MPa, more preferably at least about 1.0 MPa, and most preferably at least about 1.5 MPa. Those cured adhesives having particularly high overlap shear strength, however, are referred to as structural adhesives. "Structural adhesives" are those cured adhesives that have an overlap shear strength of at least about 3.5 MPa, more preferably at least about 5 MPa, and most preferably at least about 7 MPa.

The composition may be coated onto substrates at useful thicknesses ranging from 25-500 micrometers or more. Coating can be accomplished by any conventional means such as roller, dip, knife, or extrusion coating. Solutions of the curable composition may be used to facilitate coating. Stable thicknesses are necessary to maintain the desired coating thickness prior to crosslinking of the composition to form the crosslinked composition.

Useful substrates can be of any nature and composition, and can be inorganic or organic. Representative examples of useful substrates include ceramics, siliceous substrates including glass, metal, natural and man-made stone, woven and nonwoven articles, polymeric materials, including thermoplastic and thermosets, (such as polymethyl (meth)acrylate, polycarbonate, polystyrene, styrene copolymers, such as styrene acrylonitrile copolymers, polyesters, polyethylene terephthalate), silicones, paints (such as those based on acrylic resins), powder coatings (such as polyurethane or hybrid powder coatings), and wood; and composites of the foregoing materials.

The instant disclosure further provides a pressure sensitive adhesive which comprises a coating of the uncured or partially cured benzoxazine composition on a suitable substrate, such as an adhesive tape backing A preferred method of preparing a pressure sensitive adhesive article comprises partially curing the novel composition to a useful coating viscosity, coating the partially crosslinked composition onto a substrate (such as a tape backing) and further curing the composition. Useful coating viscosities are generally in the range of 500 to 10,000 cps.

Materials

XU3560™ benzoxazine is bis(3-phenyl-3,4-dihydro-2H, 3-benzoxazinyl)isopropane, a bisphenol-derived benzoxazine, available from Huntsman Corporation, The Woodlands Tex. Jeffamines™ D230, D400, and D2000 are poly(oxyalkylenes) terminal diamines having molecular weights of about 230, 400 and 2000, respectively. Jeffamine™ T403 is a poly(oxyalkylenes) terminal triamine having molecular weights of about 403. All Jeffamines™ were obtained from Huntsman Corporation.

PTMP (pentaerythritol tetrakis(3-mercaptopropionate), and TMMP (trimethylolpropane tris-3-mercaptonpropionate) were obtained from Evans Chemetics LP, 33 Wood Avenue South Iselin N.J. 08830.

KarenzMT™ NR-1 (1,3,5-Tris(3-melcaptobutyloxethyl)-1, 3,5-triazine-2,4,6(1H,3H,5H)-trione) and KarenzMT™ PE1 (Pentaerythritol tetrakis (3-mercaptobutylate) were obtained from Fine Chemicals Group, Specialty Chemicals Department, Showa Denko K.K., Tokyo, Japan TMMP (trimethylolpropane tris-3-mercaptopropionate) was obtained from SC Organic Chemical Subsidiary, Sakai Chemical, Osaka, Japan.

PETG a terephtalate copolymer of polyethylene glycol and cyclohexanedimethanol), was obtained from Yodo Kagaku, Fukui, Japan IOTGA (isooctyl ester of the thioglycolic acid) was obtained from Tokyo Kasei America Company, 9211 N. Harborgate Street, Portland, Oreg. 97203, U.S.A.

Paraformaldehyde was obtained from Aldrich Chemical Company, Milwaukee, Wis.

p-chlorothiophenol was obtained from Aldrich Chemical Company, Milwaukee, Wis.

Benzyl mercaptan was obtained from Aldrich Chemical Company, Milwaukee, Wis.

ortho-durene α-1,α-2 dithiol was obtained from Aldrich Chemical Company, Milwaukee, Wis.

SMS-042™-Mercaptopropyl)methylsiloxane-dimethylsiloxane copolymer was obtained from Gelest, Inc., Morrisville, Pa.

PREPARATIVE EXAMPLE 1-3

Benzoxazine A

A benzoxazine derived from a poly(ethylene oxide) diamine was prepared by combining a mixture of D-400™ diamine (215 grams, 0.5 mol), paraformaldehyde (66 grams, 2.2 mol,) and phenol (94 grams, 1 mol, Aldrich) in a 2 L round bottom flask, equipped with a reflux condenser. To this was added approximately 300 ml of chloroform, then the mixture was heated to a reflux for 10 hours. The reaction mixture was allowed to cool and the solvent and the water of condensation were removed under reduced pressure. The resulting product (approx 320 grams) was a very viscous yellow liquid.

Using the same procedure Benzoxazines B and C were prepared from the diamine Jeffamine™ D230 and the triamine Jeffamine™ T403, respectively.

EXAMPLE 1

To Benzoxazine A (0.666 grams, 0.001 mol), IOTGA (0.409 grams, 0.002 mol) were added neat at room temperature and stirred in a metal cup. The characteristic mercaptan odor disappeared immediately upon stirring. An aliquot of the thus obtained substance was dissolved in deuterated chloroform (CDCl$_3$) and the ring opened structure, below, was confirmed by $^1$H and $^{13}$C NMR.

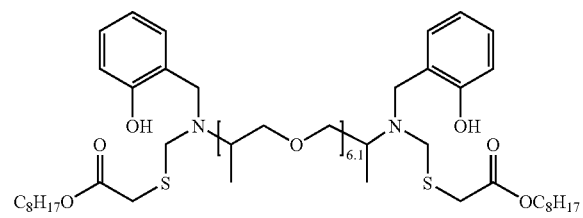

EXAMPLE 2

To XU3560™ bisphenol-A-based benzoxazine (0.462 grams, 0.001 mol) in a metal cup was added IOTGA, (0.409 grams, 0.002 mol,). The cup was placed onto a hotplate at 100° C. and stirred for approximately a minute as the benzoxazine melted. The characteristic mercaptan odor disappeared immediately upon stirring. An aliquot of product was dissolved in deuterated chloroform (CDCl$_3$) and the ring opened structure, below, was confirmed by $^1$H and $^{13}$C NMR:

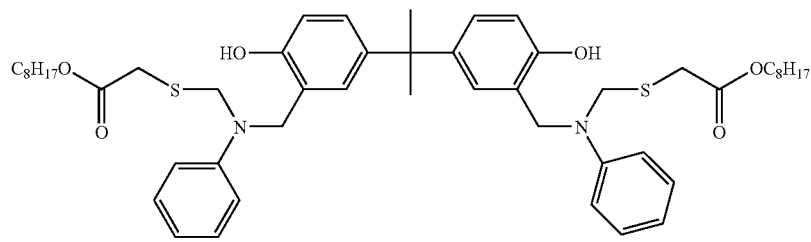

EXAMPLE 3

To Benzoxazine A (3.33 g, 0.005 mol) heated at 100 C in a metal cup to reduce its viscosity, was added p-chlorothiophenol (1.44 g, 0.01 mol, Aldrich). The cup was placed onto a hotplate at 100 C and stirred for approximately a minute as the thiophenol melted. The characteristic mercaptan odor disappeared immediately upon stirring. An aliquot of thus substance produced was dissolved in deuterated chloroform (CDCl$_3$) and the ring opened structure, below, was confirmed by $^1$H and $^{13}$C NMR:

ture and stirred. A dramatic color change from yellow to blood red wherever the two reactants come into contact, and some viscosity increase was observed. To aid the mixing, the reaction mixture was then placed on a hot plate at 100 C. The reaction yields a dark ruby red liquid. An aliquot of thus substance produced was dissolved in deuterated chloroform (CDCl$_3$) and the ring opened structure, below, was confirmed by $^1$H and $^{13}$C NMR:

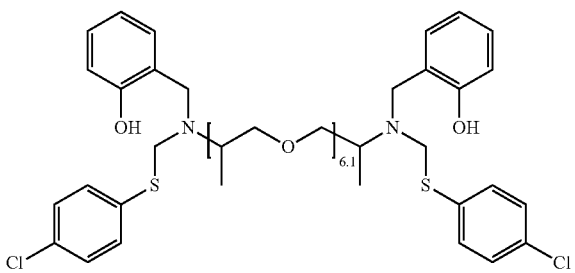

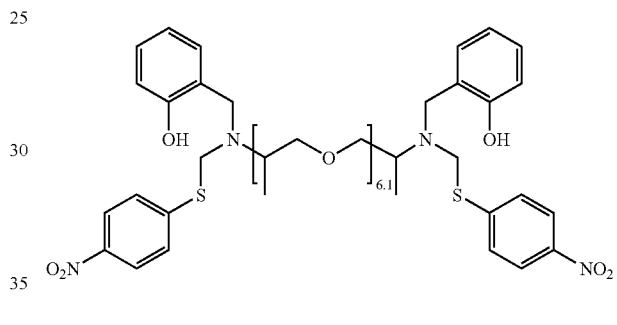

EXAMPLE 4

To Benzoxazine A (3.33 grams, 0.005 mol) heated at 100 C in a metal cup to reduce its viscosity, was added benzyl mercaptan (1.24 grams, 0.01 mol,). The cup was placed onto a hotplate at 100 C and stirred for approximately a minute. The characteristic mercaptan odor disappeared immediately upon stirring. An aliquot of thus substance produced was dissolved in deuterated chloroform (CDCl$_3$) and the ring opened structure, below, was confirmed by $^1$H and $^{13}$C NMR

EXAMPLE 6

2.68 grams of SMS-042(Mercaptopropyl)methylsiloxane-dimethylsiloxane copolymer (Gelest) was added to Benzoxazine A (0.333 grams, 0.0005 mol) in a metal cup on a hotplate and heated at 100 C. temperature while stirring. The mixture phase separated producing an increasingly thicker and eventually rubbery, opaque yellowish mass.

EXAMPLE 7

α-1, α-2 dithiol ortho-durene (0.816 grams, 0.00424 mol, 97% Aldrich) were added to XU3560™ bisphenol-A based benzoxazine (1.959 grams, 0.00424 mol) in a 100 ml round bottom flask equipped with a condenser and dissolved in toluene. Two drops of acetic acid were added to catalyze the reaction. The reaction was heated to reflux for 8 hours. The solvent was removed using a water azeotrope in a rotary evaporator to yield yellowish-orange product. An aliquot was dissolved in warm deuterated dimethyl sulfoxide (dmso-d6), and the ring opened polymeric structure, below, was confirmed by $^1$H NMR. Another aliquot of the polymer was partially soluble in dimethyl formamide (DMF). The DMF-soluble fraction was analyzed using gel-permeation chromatography (GPS) to provide an approximate molecular weight Mw of 62,000 daltons for the soluble fraction.

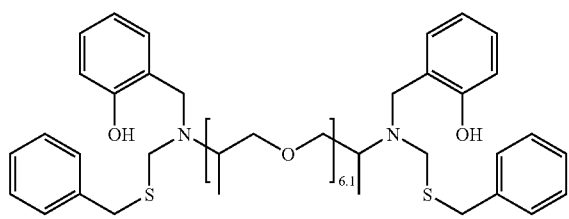

EXAMPLE 5

To Benzoxazine A (3.33 grams, 0.005 moles) p-nitrothiophenol (1.55 g, 0.01 mol) were added at room tempera-

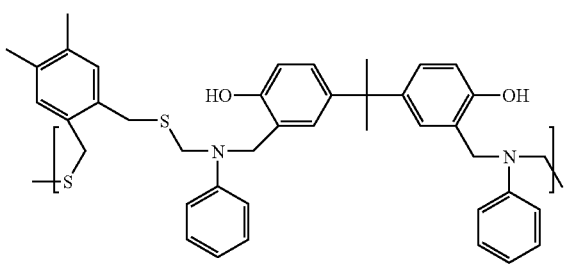

EXAMPLE 8

1.37 gram of 4-chloro 1,3 benzene dithiol (98%, 0.0079 mol, Aldrich) was added to a round bottom flask, equipped with a condenser, followed by approximately 20 ml of toluene and XU-3560 bisphenol-A based benzoxazine (3.65 grams 0.0079 mol, Huntsman). Two drops of acetic acid were added to catalyze the reaction. The flask was heated to reflux for 8 hour during which the solution turned progressively darker yellow, and yellow precipitate formed on the walls of the reaction flask. The solvent was removed using a water azeotrope in a rotary evaporator to yield a bright yellowish-orange product. An aliquot of the product was dissolved in warm deuterated dimethyl sulfoxide (dmso-d6), and thus the ring opened polymeric structure, below, was confirmed by $^1$H NMR. A dimethylformamide-soluble fraction was analyzed using gel-permeation chromatography (GPS) to provide an approximate molecular weight Mw of 10,000 daltons for the soluble fraction.

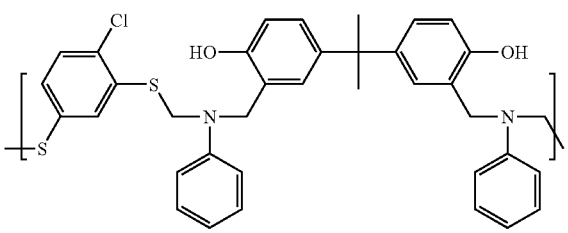

EXAMPLE 9

Benzoxazine A (3.33 grams, 0.005 mol) was heated with 5.5 grams of water in a metal cup on a hot plate at 100 C and stirred hot. The contents were allowed to cool to room temperature and then PTMP (1.22 grams 0.0025 mol) were added and stirred. The mixture thickened gelled in approximately the same time (less than 1 minute) as without water under room temperature conditions. The example illustrates that the benzoxazine-thiol reaction can take place in presence of and even under water without any apparent effect thereof on the polymerization.

EXAMPLE 10

A 0.396 gram sample of the material prepared in Example 9 was placed into a vial of water (approximately 10 ml). The vial was capped and placed into a 95° C. oven for 24 hours. After 24 hours the sample was extracted, paper towel dried and re-weighed. The new mass was found to be 0.401 grams. After 12 hours in open air the mass equilibrated to 0.395 grams. The example demonstrates that benzoxazine-thiol adducts are effective moisture barriers.

EXAMPLE 11

KarenzMT-NR1 (1.89 grams, 0.0033 mol) was admixed with XU-3560 (2.31 grams, 0.005 mol) in a metal cup. Two drops of acetic acid were added, and the mixture was deposited in a rectangular silicone rubber mold, sandwiched between two silicone release liner coated PET sheets and pressed between glass plates. The mold consisted of 10~1 mm thick sheet with rectangular cutouts (approximately 5 mm wide×30 mm long) to prepare samples for the dynamic mechanical analysis.

The clamped construct was then placed in an oven at 130° C. for 30 minutes. The assembly was then allowed to cool to room temperature. Shiny, transparent lemon-yellow samples was obtained. The samples were brittle and glassy. Dynamic mechanical analysis was run in Seiko DMA in tensile mode at the temperature range between −50 and 220° C. After the run was completed, the sample was removed, examined visually and repositioned for the subsequent DMA run. Ultimately, the samples were cycled 4 times between −50 and 220° C. with the heating rate of 2° C./min. The samples did not noticeably darken with each run, and remain transparent. The traces of the loss tangent of the DMA scans are shown in FIG. 1 as curves 1-4.

EXAMPLE 12

PETG (1.08 grams, 0.0025 mol) was admixed to Benzoxazine A (3.33 grams, 0.005 mol) in a metal cup at room temperature. Upon stirring, the mixture gels within 10 seconds. The resulting material was a translucent grayish rubber, sticky to the touch. When placed into an oven at 130° C., the material lost some of its tack, but remained rubbery.

EXAMPLE 13

50 grams of XU-3560 benzoxazine was admixed with 50 grams of Benzoxazine A in a metal can. The can was placed into an oven at 130° C. for 30 minutes and stirred while cooling to form a melt solution of the two benzoxazine compounds. 20 grams (0.073 mol benzoxazine equivalents) of that mixture was heated to ca. 70° C. and to it was added TMMP (9.752 grams, 0.073 mol thiol equivalents). The characteristic mercaptan odor disappeared immediately upon stirring. Upon mixing the viscosity, which initially dropped, started to increase after approximately a minute of mixing. An aliquot of the reaction product was dissolved in deuterated chloroform and the ring opened structure was confirmed by IH and 13 C NMR for the aliphatic fraction derived from Benzoxazine A, while the aromatic fraction derived from benzoxazine XU-3560 of the benzoxazine appeared unreacted as NMR showed the oxazine ring still closed.

EXAMPLE 14

Cohesive Strength Method (Lap Shear Strength Testing)

Lap shear specimens were made using 4"×7"×0.063"7075 T6 bare aluminum that had been anodized according to Boeing Aircraft Company Specification BAC-5555. The anodization voltage was 22.5 volts. The specimen was generated as described in ASTM Specification D-1 002-05.

A strip of approximately Y;"×10 mils of the benzoxazine-thiol adduct, prepared in Example 13 was applied to one edge of each of the two anodized aluminum adherends using a scraper. Three 5 mil diameter piano wires were used as spacers for bondline thickness control. The bond was closed and taped on the edge. The bond was placed between sheets of aluminum foil and pieces of cardboard. Two 14# steel plates were used to apply pressure to provide for adhesive spreading. The assembly was placed into an oven heated to 130° C. for 1 hour. After the adhesive had been allowed to cool to room temperature, the larger specimen was cut into 1" wide samples, providing a Y; square inch bonded area. Six lap shear samples were obtained from each larger specimen. The bonds were tested to failure at room temperature on a Sintech Tensile Testing machine using a crosshead displacement rate of 0.1"/min. The failure load was recorded. The lap width was measured with a vernier caliper. The lap shear strengths are calculated as (2× failure load)/measured width. The average and standard deviation were calculated from the results of six tests. The lap shear strength was 2174 lbs/in2 (~15 MPa)-21-.

T-Peel Test Method

T-peel values were measured using 4"×8"×0.025" 7075 T6 bare aluminum that had been anodized as described above. The test was as described in ASTM D-1876; Standard Test Method for Peel Resistance of Adhesives (T-Peel Test," Annual Book of ASTM Standards, vol. 15.06, pp. 115-117 (1995). A strip of approximately 2"×5"×10 mil of adhesive prepared in the Example 13 was applied to both of the two anodized aluminum adherends. 10 mil thick spacers made from brass shims were applied to the edges of the bonded area for bondline thickness control. The bond was closed and adhesive tape was applied to hold the adherends 10 together during the cure. The adhesive bonds were placed between sheets of aluminum foil and also between pieces of cardboard. Four 14 pound steel plates were used to apply pressure to provide for adhesive spreading. The assembly was placed into an oven heated to 130° C. for 1 hour. After the adhesive had been allowed to cool to room temperature, the larger 15 specimen was cut into 1" wide samples, yielding two 1" wide specimens. The bonds were tested to failure at room temperature on a Sintech Tensile Testing machine using a crosshead displacement rate of 12"/min. The initial part of the loading data was ignored. The average load was measured after about 1" was peeled. The T-peel strength is the average of three peel measurements was 2.2 lbf/in (3.8 N/cm).

Overlap Shear Strength

Overlap Shear Strength was determined using a maple wood substrate as follows. A 0.5 gram (.+-.0.05 grams) quantity of the hot melt composition to be tested was preheated in a sealed cartridge at 250.degree. F. (121.degree. C.) for between 30 and 60 minutes prior to extruding it onto one end portion of a 1 inch (2.5 cm) wide by 4 inch (10 cm) long by 0.31 inch (0.8 cm) thick section of a smooth maple wood panel (available from Martin Lumber, St. Paul, Minn.). The wood substrate had been previously conditioned for 7 days at about 77.degree. F. (25.degree. C.) and 50% relative humidity. After the adhesive was applied, 0.003-0.005 inch (0.08-0.13 mm) diameter glass beads were sparingly sprinkled uniformly on the molten adhesive to control bondline thickness. An overlap bond was then formed in the lengthwise direction by immediately mating the substrate with another piece of maple to provide a 0.5 inch by 1.0 inch (1.25 by 2.5 cm) overlap bond area. Firm hand pressure was applied to compress the adhesive to a thickness of 0.003-0.005 inches (0.08-0.13 mm) and to squeeze excess adhesive from the bond area.

The test assembly was not moved for between 5 and 10 minutes. Excess flash (if present) was trimmed from the bottom side of the assembly.

At this point a bond had formed and the initial overlap shear strength was measured. The bonded substrates were allowed to cure at about 77.degree. F. (25.degree. C.) and 50% relative humidity for various periods of time before testing for overlap shear strength.

The resulting test coupon was tested for overlap shear strength at a crosshead speed of 2 inches/minute (5.1 centimeters/minute) using a SINTECH 10 Tensile Tester (available from MTS Systems Corporation, Eden Prairie, Minn.). Three test coupons were evaluated, the load values obtained were multiplied by 2 to normalize to a 1 square inch overlap area, and an average value for overlap shear strength was calculated. The results are reported in pounds per square inch (psi) (MegaPascals, MPa). In one embodiment, a value of 1000 psi after 24 hours was desired.

EXAMPLE 15

Benzoxazine composition employed in Example 13 was loaded with 17% silicone core shell toughener by Kaneka Texas Corporation. To 19.33 grams (0.059 mol BZ) of that material TMMP was admixed (7.8 grams, 0.059 mol thiol). The resulting material 25 was coated onto aluminum adherents as in the previous Examples. The following adhesive data were obtained:

| XU3560/JD400BZ/CST/TMMP | Overlap Shear | T-peel |
|---|---|---|
| Average Value | 1472 lbs/in2 | 5.2 lb/in |
| STD | 48 | 1.2 |

What is claimed is:

1. The reaction product of a benzoxazine with a thiol of the formula:

$R^6$—[$(CO_2)_x$—$R^7$—SH]$_y$, wherein $R^6$ is a non-polymeric aliphatic, cycloaliphatic, aromatic or alkyl-substituted aromatic moiety having from 1 to 30 carbon atoms and optionally 1 to four catenary heteroatoms of oxygen, nitrogen or sulfur; wherein $R^7$ is a divalent hydrocarbyl group, x is 0 or 1, y is 1 to 6.

2. The reaction product of claim 1 wherein the thiol is of the formula:

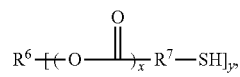

wherein $R^6$ is a non-polymeric aliphatic, cycloaliphatic, aromatic or alkyl-substituted aromatic moiety having from 1 to 30 carbon atoms and optionally 1 to four catenary heteroatoms of oxygen, nitrogen or sulfur; wherein $R^7$ is a divalent hydrocarbyl group, x is 0 or 1, y is 1 to 6.

3. The reaction product of claim 1 wherein the thiol is of the formula:

$$R^6\!-\!\!\left[\!\!\left(\underset{\|}{\overset{O}{C}}\!-\!O\right)_{\!x}\!\!-\!R^7\!-\!SH\right]_{\!y},$$

wherein
R$^6$ is a non-polymeric aliphatic, cycloaliphatic, aromatic or alkyl-substituted aromatic moiety having from 1 to 30 carbon atoms and optionally 1 to four catenary heteroatoms of oxygen, nitrogen or sulfur; wherein
R$^7$ is a divalent hydrocarbyl group,
x is 0 or 1,
y is 1 to 6.

4. The reaction product of claim 1 wherein the thiol is of the formula:

$$R^6\!-\!\!\left[R^7\!-\!SH\right]_{y}$$

wherein
R$^6$ is a non-polymeric aliphatic, cycloaliphatic, aromatic or alkyl-substituted aromatic moiety having from 1 to 30 carbon atoms and optionally 1 to four catenary heteroatoms of oxygen, nitrogen or sulfur; wherein
R$^7$ is a divalent hydrocarbyl group,
x is 0 or 1,
y is 1 to 6.

5. The reaction product of claim 1 wherein R$^7$ is a divalent alkylene.

6. The reaction product of claim 1, wherein the benzoxazine is a polybenzoxazine.

7. The reaction product of claim 1 wherein the thiol is a polythiol.

8. The reaction product of claim 6 wherein the polybenzoxazine is of the formula:

wherein
each of R$^1$ is H or an alkyl group;
R$^2$ is H, a covalent bond, or a polyvalent (hetero)hydrocarbyl group;
R$^5$ is the (hetero)hydrocarbyl residue of a primary amino compound having a valence of x, and
x is at least 1.

9. The reaction product of claim 1 wherein the benzoxazine is of the formula:

wherein
each of R$^1$ is H or an alkyl group;
R$^2$ is H, a covalent bond, or a divalent (hetero)hydrocarbyl group;
R$^5$ is the divalent (hetero)hydrocarbyl group.

10. The reaction product of claim 9 wherein R$^5$ is a poly(alkyleneoxy) group.

11. The reaction product of claim 1 wherein the benzoxazine is of the formula:

each of R$^1$ is H or an alkyl group;
R$^2$ is H, a covalent bond, or a divalent (hetero)hydrocarbyl group;
R$^5$ is the (hetero)hydrocarbyl group.

12. The reaction product of claim 1 wherein the benzoxazine is of the formula:

wherein,
each of R$^1$ is H or an alkyl group;
R$^2$ is a covalent bond, or a divalent (hetero)hydrocarbyl group;
R$^5$ is the divalent (hetero)hydrocarbyl residue of a primary diamino compound, and z is at least 2.

13. The reaction product of claim 1, where the benzoxazine is derived from the reaction product of a phenol, an aldehyde and a primary amine.

14. The reaction product of claim 1, where the benzoxazine is derived from the reaction product of a bisphenol, an aldehyde and a primary amine.

15. The reaction product of claim 1, where the benzoxazine is derived from the reaction product of phenol, an aldehyde and a polyamine.

16. The reaction product of claim 15, wherein the polyamine is a poly(ethyleneoxy) diamine.

17. The reaction product of claim 1 comprising a polymer of the formula:

wherein
R¹ is H or an alkyl group;
R² is H, a covalent bond, or a divalent (hetero)hydrocarbyl group;
R⁴ is a hydrocarbyl group of valence n and n is 2 to 6;
R⁵ is a (hetero)hydrocarbyl group, and y is at least 2.

18. The reaction product of claim 1 comprising a compound of the formula:

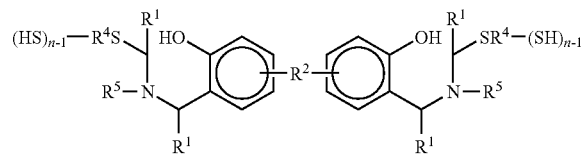

wherein
R¹ is H or an alkyl group, and is the residue of an aliphatic aldehyde;
R² a covalent bond, or a divalent (hetero)hydrocarbyl group;
R⁴ is hydrocarbyl group of valence n and n is 1 to 6;
R⁵ is a (hetero)hydrocarbyl group.

19. The reaction product of claim 1 comprising a compound of the formula:

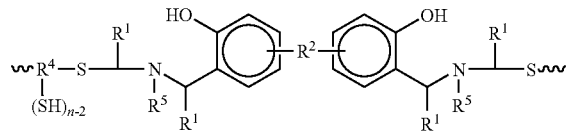

R¹ is H or an alkyl group, and is the residue of an aliphatic aldehyde;
R² is a covalent bond, or a divalent (hetero)hydrocarbyl group;
R⁴ is hydrocarbyl group of valence n and n is 2 to 6;
R⁵ is the (hetero)hydrocarbyl group.

20. The reaction product of claim 1 comprising a compound of the formula:

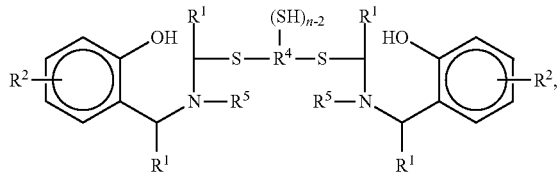

where
each R¹ is H or an alkyl group, and is the residue of an aliphatic aldehyde,
R² is a covalent bond, a H, or a divalent (hetero)hydrocarbyl group;
R⁴ is hydrocarbyl group of valence n, and n is 2 to 6;
R⁵ is the (hetero)hydrocarbyl group.

21. The reaction product of claim 1 comprising a polymer of the formula:

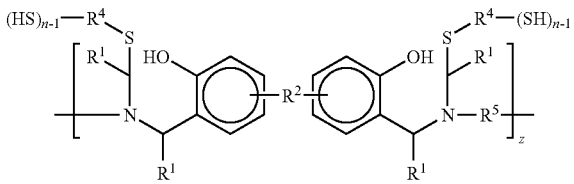

wherein
each R¹ is H or an alkyl group,
R² is a covalent bond, or a divalent (hetero)hydrocarbyl group;
R⁴ is a hydrocarbyl group of valence n and n is 2 to 6;
R⁵ is the (hetero)hydrocarbyl group; and
z is at least 2.

* * * * *

UNITED STATES PATENT AND TRADEMARK OFFICE
CERTIFICATE OF CORRECTION

PATENT NO. : 8,389,758 B2
APPLICATION NO. : 12/685703
DATED : March 5, 2013
INVENTOR(S) : Ilya Gorodisher It is certified that error appears in the above-identified patent and that said Letters Patent is hereby corrected as shown below:

In the Specification

Column 6,
Line 51, delete "propane diamine;" and insert -- propanediamine; --.

Column 8,
Line 1-9, delete " 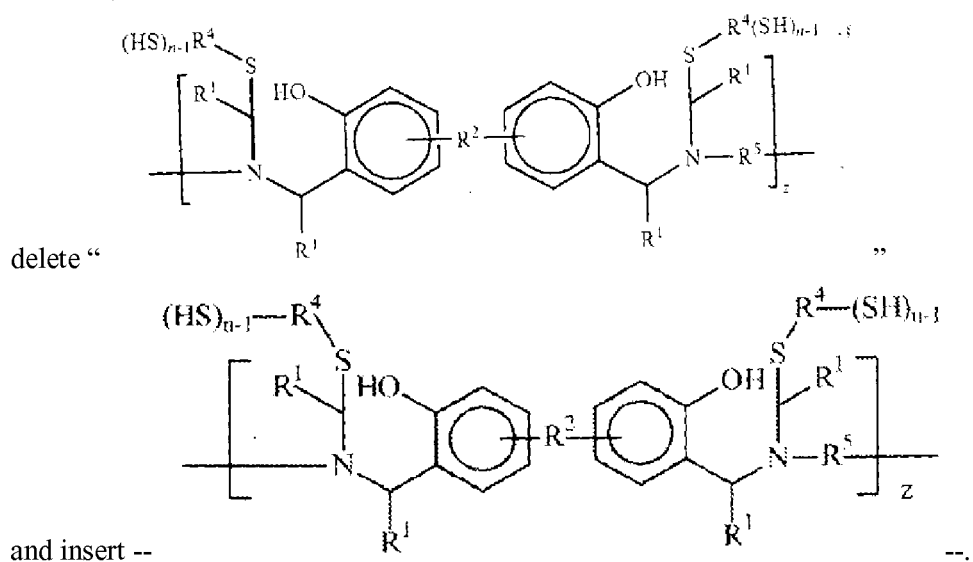 "

and insert -- --.

Column 13,
Line 30, delete "backing A" and insert -- backing. A --.

In the Claims

Column 23,
Line 21, after "$R^2$" insert -- is --.

Signed and Sealed this
Ninth Day of July, 2013

Teresa Stanek Rea
*Acting Director of the United States Patent and Trademark Office*